United States Patent [19]
Marx

[11] 3,966,825
[45] June 29, 1976

[54] PROCESS FOR PREPARING β-NITROETHANETHIOL

[75] Inventor: Michael Marx, Sunnyvale, Calif.

[73] Assignee: Syntex (U.S.A.) Inc., Palo Alto, Calif.

[22] Filed: June 30, 1975

[21] Appl. No.: 591,596

[52] U.S. Cl. .......................... 260/609 R; 260/954; 260/488 R; 260/632 N; 260/481 R
[51] Int. Cl.² .................................. C07C 149/14
[58] Field of Search ............ 260/609 A, 954, 488 R, 260/632 N, 481 R

[56] References Cited
UNITED STATES PATENTS 2,351,763   6/1944   Hull ............................. 260/609 A

*Primary Examiner*—Lewis Gotts
*Assistant Examiner*—D. R. Phillips
*Attorney, Agent, or Firm*—Tom M. Moran; William B. Walker

[57] ABSTRACT

β-Nitroethanethiol is prepared by reacting a carboxylic acid ester of β-nitroethananol with trisodium thiophosphate and hydrolyzing the resulting thiophosphate ester to form β-nitroethanethiol.

8 Claims, No Drawings

PROCESS FOR PREPARING β-NITROETHANETHIOL

BACKGROUND OF THE INVENTION

1. Field of The Invention

This invention relates to a process for preparing β-nitroethanethiol. The compound has been discovered to be useful in the novel synthesis of biotin as described in U.S. Pat. application Ser. No. 591,597 for Preparing Biotin (M. Marx and J. Reisdorff) filed June 30, 1975.

Prior Art

The compound β-nitroethanethiol is known in the prior art (see for example R. L. Heath and A. Lambert, J. Chem. Soc., 1477[1947]). Past attempts to prepare β-nitroethanethiol [IV] from a readily available starting material, e.g. β-nitroethanol, [I] have resulted in yields of at best about 10%, and have necessitated isolation of the highly reactive intermediate nitroethylene [III] (cf., inter alia, the reference cited above). For example, reaction of β-nitroethyl acetate [II] with potassium hydrogen sulfide leads exclusively to bis-nitroethyl sulfide [V] rather than to β-nitroethanethiol, [IV] and even the reaction of purified nitroethylene (prepared in ~50% yield from β-nitroethanol) with hydrogen sulfide is reported to produce only 18% of β-nitroethanethiol accompanied by 48% of the aforementioned bis-nitroethyl sulfide. These reactions and the intermediates are set forth in the reaction scheme following.

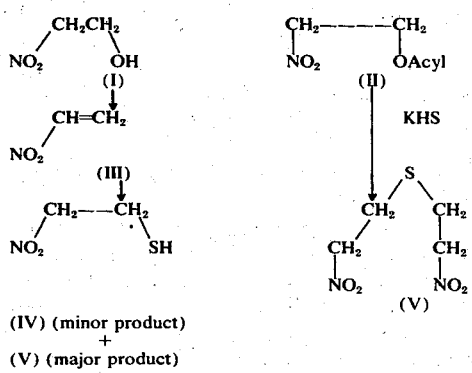

(IV) (minor product)
+
(V) (major product)

We have discovered a novel method for preparing nitroethanethiol in significant yields using an elegantly simple process.

SUMMARY OF THE INVENTION

The process of this invention comprises reacting a carboxylic acid ester of β-nitroethanol with trisodium thiophosphate, followed by acid hydrolysis of the resulting thiophosphate ester to form the desired product nitroethanethiol, designated as structure IV in the reaction scheme below. Preferably, the ester is β-nitroethyl acetate which is prepared by reacting acetic acid with nitroethanol. The overall reaction scheme is set forth in the following series of reactions:

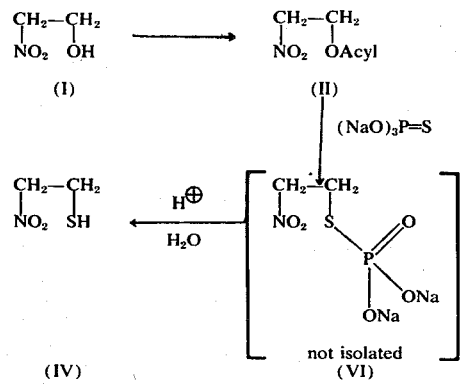

Preferred Embodiments

As pointed out under "Field of the Invention," above, β-nitroethanethiol is useful in the novel synthesis of biotin. In that process β-nitroethanethiol is reacted with a lower alkyl ester of 7-nitro-hept-6-enoic acid to form a lower alkyl ester of dl-7-thia-6-nitro-methyl-9-nitro-nonanoic acid according to the following reaction scheme

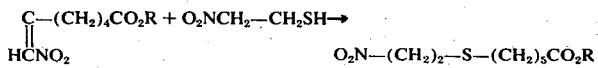

wherein R is alkyl of 1 to 4 carbons. A more complete discussion is found in patent application, U.S. Ser. No. 591,597, filed June 30, 1975, and as much of that patent application as is pertinent is incorporated herein by reference.

The essence of this invention requires the reaction of trisodium thiophosphate with a suitable carboxylic acid ester of β-nitroethanol (shown in structure II), followed by acid hydrolysis, to form the nitroethanethiol. The ester may be the β-nitroethanol ester of any suitable aliphatic or aromatic hydrocarbon carboxylic acid having from 1 to 12 carbon atoms. Representative of the carboxylic acids are aliphatic carboxylic acids such as acetic acid, propionic acid, butanoic acid, pentanoic acid, hexanoic acid, heptanoic acid, octanoic acid, nonanoic acid, decanoic acid, undecanoic acid and the like. Suitable aromatic acids include benzoic acid, p-nitrobenzoic acid, 3,5-dinitrobenzoic acid, p-methyl benzoic acid, and the like. Acetic acid has been found to be particularly suitable.

The β-nitroethyl ester may be formed by reacting β-nitroethanol with a suitable acylating agent such as the carboxylic acid itself or derivatives of the acids such as acid chlorides or anhydrides. Eminently suitable as the acylating agent is an aliphatic acid of 2-4 carbon atoms. Preferably the aliphatic acid reacted with the β-nitroethanol is acetic acid. Generally, the reaction may take place in any suitable solvent under conditions sufficient to form the desired ester. The solvents may be any aprotic, nonpolar hydrocarbon solvents such as an aliphatic or aromatic solvent. Representative aliphatic solvents include those having 6–12 carbon atoms such as hexane, heptane, octane, nonane, decane and dodecane, while suitable aromatic solvents include toluene, benzene, xylene, and the like. Hexane has been found to be particularly valuable.

Generally, the acetic acid and the nitroethanol are refluxed together in the presence of a suitable acid catalyst such as sulfuric acid. The resulting water of reaction is separated and collected. Generally, the reaction takes place over a period of about 10 hours but preferably will be finished in less than 8 hours.

The reaction of the resulting ester with trisodium thiophosphate takes place in a suitable solvent, preferably an aqueous medium in which the trisodium thiophosphate is dissolved. Reaction takes place readily at low temperatures, that is, temperatures of about 0° to 40°C, preferably about 15° to 25°C. The reaction procedure involves dissolving the trisodium thiophosphate in a suitable amount of water and slowly adding the carboxylic acid ester of β-nitroethanol to the water solution while thoroughly stirring the solution. This results in an intermediate phosphate ester of β-nitroethanoethiol shown as structure VI in the above reaction scheme under "Summary of the Invention." Since the reaction appears to take place in a 2-phase system, it is preferable to add a suitable surfactant to aid in the reaction. Suitable surfactants include cetyltrimethylammonium chloride and benzyltriethylammonium chloride, preferably the latter. The reaction will require no more than a period of about 20 hours or less for completion, preferably less than 16 hours. When the reaction is sufficiently advanced, the aqueous solution is acidified with a suitable acid such as sulfuric or hydrochloric acid to hydrolyzes the ester designated as structure VI above at about 30° to 50°C, preferably about 40°C for a suitable period of time, about 2 hours or less. The intermediate ester (VI) need not be isolated by this simple method.

The following example is given to more fully describe the process of the invention to one skilled in the art and to set forth a particularly valuable set of process variables. The example merely sets forth representative conditions and reactants and is not to be interpreted as limiting the scope of the invention set forth in the appended claims.

EXAMPLE I

A. Preparation of Nitroethanol

80 G. dry paraformaldehyde were suspended in 1.6 nitromethane ($CH_3NO_2$). After addition of 3 ml. of 3 N potassium hydroxide (KOH) in methanol the suspension was stirred for 30 minutes. The now clear solution was acidified with 1.5 ml. conc. sulfuric acid, stirred for an additional 30 min. and filtered. The excess $CH_3NO_2$ was distilled off at 30°–50°C bath temperature and the residue distilled at about 1mm/50°C yielding 106 g. colorless nitroethanol.

B. Preparation of β-Nitroethylacetate

64 G. of nitroethanol, 50 ml. glacial acetic acid, 250 ml. benzene and 5 drops conc. $H_2SO_4$ were refluxed, using a water separator for 8 hours; 12 ml. of $H_2O$ were collected. The solution was evaporated and vacuum distilled (1 mm. Hg at 60°C) yielding 89 g. colorless β-nitroethylacetate.

C. Preparation of Trisodium Thiophosphate

80 G. sodium hydroxide were dissolved in 500 ml. water and 35 ml. phosphorous thiochloride ($PSCl_3$, 98%) were added to maintain the reaction temperature between 75° and 85°C (ca. 30 min.). The reaction was stirred at 80°C until all the $PSCl_3$ had reacted (45 min.). Then the reaction mixture was put into the refrigerator (0°C) overnight. The precipitated white crystals were filtered off and washed with 100 ml. EtOH. The crystals were dissolved in 250 ml. distilled water at 45°C and reprecipitated by the slow addition of 200 ml. ethanol (EtOH) under rapid stirring. The solution was cooled to room temperature filtered and the white crystals were washed with 100 ml. EtOH.

The resulting product was dehydrated by stirring in 600 ml. absolute MeOH for 1 ½ hours. The fine white powder was filtered off and dried at 105°C (vacuum) for 1 hour yielding 38 g. (59%) of anhydrous trisodium thiophosphate ($Na_3PO_3S$).

D. Preparation of Nitroethanethiol

To a solution of 54.3 g. $Na_3PO_3S$ in 600 ml. distilled water were added 0.5 g. benzyltriethylammonium chloride, the mixture cooled to 15° and then 39.9 g. β-nitroethylacetate, prepared above, was added during 15 min., the temperature being maintained below 20°C. The mixture was stirred at room temperature for 16 hours, then acidified with 60 ml. conc. HCl and hydrolyzed at 40° for 1 hour. The crude reaction product mixture was taken up in ethyl acetate and washed with aqueous saturated sodium chloride solution. The organic layer was dried over magnesium sulfate and evaporated using a laboratory rotary evaporator. The residue was distilled yielding 9.7 g. (30%) β-nitroethanethiol b.p. 37°–39° (0.3 mm).

What is claimed is:

1. The process for preparing β-nitroethanethiol which comprises reacting a carboxylic acid ester of β-nitroethanol with trisodium thiophosphate followed by acid hydrolysis of the resulting phosphate ester of β-nitroethanethiol.

2. The process of claim 1 wherein said carboxylic acid ester is β-nitroethyl acetate.

3. The process of claim 2 wherein the reaction takes place in an aqueous medium.

4. The process of claim 3 wherein a suitable surfactant is added to the water.

5. The process of claim 4 wherein said surfactant is chosen from the group comprising benzyltriethylammonium chloride and cetyltriethylammonium chloride.

6. The process of claim 1 wherein said carboxylic acid ester is prepared by acylating β-nitroethanol.

7. The process of claim 6 wherein said ester is prepared by reacting β-nitroethanol with acetic acid.

8. The process for preparing nitroethanethiol which comprises a. reacting acetic acid and β-nitroethanol to form β-nitroethyl acetate;
b. reacting β-nitroethyl acetate with trisodium thiophosphate; and
c. effecting hydrolysis of the resulting phosphate ester under acid conditions to form β-nitroethanethiol.

* * * * *